US00PP28251P2

(12) United States Plant Patent
Koekkoek

(10) Patent No.: US PP28,251 P2
(45) Date of Patent: Aug. 8, 2017

(54) CARNATION PLANT NAMED 'HILREES'

(50) Latin Name: *Dianthus caryophyllus*
Varietal Denomination: Hilrees

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 43 days.

(21) Appl. No.: 14/545,370

(22) Filed: Apr. 28, 2015

(51) Int. Cl.
*A01H 5/02* (2006.01)

(52) U.S. Cl.
USPC ..... Plt./273

(58) Field of Classification Search
USPC ..... Plt./273
See application file for complete search history.

(56) References Cited

PUBLICATIONS

UPOV hit on *Dianthus* plant named 'Hilrees', QZ PBR 20143566, published Dec. 23, 2014.*

* cited by examiner

*Primary Examiner* — Anne Grunberg
(74) *Attorney, Agent, or Firm* — C. A. Whealy

(57) ABSTRACT

A new and distinct cultivar of Carnation plant named 'Hilrees', characterized by its compact, uniformly mounding and upright to broadly spreading plant habit; relatively small leaves; freely flowering habit; dark red purple and white bi-colored semi-double flowers; and good container performance.

1 Drawing Sheet

Botanical designation: *Dianthus caryophyllus.*
Cultivar denomination: 'HILREES'.

BACKGROUND OF THE INVENTION

The present invention relates to a new and distinct cultivar of Carnation plant, botanically known as *Dianthus caryophyllus*, grown commercially as a container plant and hereinafter referred to by the name 'Hilrees'.

The new Carnation plant is a product of a planned breeding program conducted by the Inventor in De Kwakel, The Netherlands. The objective of the breeding program is to create new container Carnation plants with numerous semi-double flowers.

The new Carnation plant is a naturally-occurring whole plant mutation of *Dianthus caryophyllus* 'Koes', disclosed in U.S. Plant Pat. No. 22,370. The new Carnation plant was discovered and selected by the Inventor as a single flowering plant from within a population of plants of 'Koes' in a controlled greenhouse environment in De Kwakel, The Netherlands in May, 2011.

Asexual reproduction of the new Carnation plant by terminal cuttings propagated in a controlled greenhouse environment in De Kwakel, The Netherlands since November, 2011 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilrees'. These characteristics in combination distinguish 'Hilrees' as a new and distinct Carnation plant:

1. Compact, uniformly mounding and upright to broadly spreading plant habit.
2. Relatively small leaves.
3. Freely flowering habit.
4. Dark red purple and white bi-colored semi-double flowers.
5. Good container performance.

Plants of the new Carnation differ primarily from plants of the mutation parent, 'Koes', in flower color as plants of 'Koes' have dark purple, red purple and pink-colored flowers.

Plants of the new Carnation also can be compared to plants of *Dianthus caryophyllus* 'Margarita', disclosed in U.S. Plant Pat. No. 17,335. In side-by-side comparisons, plants of the new Carnation differed primarily from plants of 'Margarita' in the following characteristics:

1. Leaves of plants of the new Carnation were shorter than leaves of plants of 'Margarita'.
2. Flowers of plants of the new Carnation were larger than flowers of plants of 'Margarita'.
3. Flower petals of plants of the new Carnation were less deeply incised than flower petals of plants of 'Margarita'.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant. The photograph comprises a side perspective view of a typical flowering plant of 'Hilrees' grown in a container.

DETAILED BOTANICAL DESCRIPTION

Plants used in the aforementioned photograph and following observations and measurements were grown during the winter in 10.5-cm containers in a glass-covered greenhouse in De Kwakel, The Netherlands and under cultural practices typical of commercial container Carnation production. During the production of the plants, day temperatures ranged from 12° C. to 15° C., night temperatures averaged 12° C. and light levels averaged 7,000 lux. Plants were pinched one time five weeks after planting. Plants used for the photograph and description were 23 weeks old. In the following description, color references are made to The Royal Horticultural Society Colour Chart, 2007 Edition, except where general terms of ordinary dictionary significance are used.

Botanical classification: *Dianthus caryophyllus* 'Hilrees'.

Parentage: Naturally-occurring whole plant mutation of *Dianthus caryophyllus* 'Koes', disclosed in U.S. Plant Pat. No. 22,370.

Propagation:

*Type*.—By terminal cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; moderately vigorous growth habit.

*Plant height, soil level to top of foliar plane*.—About 12.9 cm.

*Plant height, soil level to top of floral plane*.—About 16.2 cm.

*Plant diameter or spread*.—About 24.4 cm.

*Lateral branches*.—Branching habit: Freely branching habit with about six main (basal) stems; each main stem with about four lateral branches. Length, main stems: About 7.4 cm. Length, lateral branches: About 4 cm. Diameter, main stems and lateral branches: About 2 mm. Internode length: About 1.7 cm. Number of internodes per stem: About four. Strength: Strong. Aspect: Main stems, mostly upright; lateral branches, about 30° from the main stem. Cross-section: Angular; solid. Texture: Smooth, glabrous. Luster: Matte. Color: Close to 138B.

Leaf description:

*Arrangement*.—Opposite, simple; sessile.

*Length*.—About 8.6 cm.

*Width*.—About 7 mm.

*Shape*.—Lanceolate.

*Apex*.—Narrowly acute.

*Base*.—Attenuate; decurrent.

*Margin*.—Entire.

*Texture, upper and lower surfaces*.—Smooth, glabrous.

*Luster, upper and lower surfaces*.—Matte.

*Venation pattern*.—Parallel.

*Color*.—Developing leaves, upper surface: Close to 143A to 143B; towards the base, close to 145A. Developing leaves, lower surface: Close to 144A; towards the base, close to 145B. Fully expanded leaves, upper surface: Close to N137C; venation, same as lamina, close to N137C. Fully expanded leaves, lower surface: Close to 137A; venation, close to 144A.

Flower description:

*Flower form and flowering habit*.—Terminal semi-double flowers arranged singly, in pairs or in panicles with about five flowers each; freely flowering habit with numerous flowers developing during the flowering season; flowers face mostly upright to slightly outwardly.

*Natural flowering season*.—Flowering is continuous from the summer to late summer in The Netherlands; plants begin flowering about twelve weeks after planting.

*Postproduction longevity*.—Flowers last about ten days on the plant; flowers not persistent.

*Fragrance*.—Faintly fragrant; clove-like, sweet.

*Flower buds*.—Length: About 2.2 cm. Diameter: About 9 mm. Shape: Elliptic; styles not extruded. Color: Close to 137C; towards the base, close to 143C.

*Inflorescence height*.—About 8.6 cm.

*Inflorescence diameter*.—About 8 cm.

*Flower diameter*.—About 4.8 cm.

*Flower depth*.—About 4.2 cm.

*Petals and petaloids*.—Quantity and arrangement: About 15 petals/petaloids arranged in about three whorls. Length: About 4.2 cm. Width: About 2.1 cm. Shape: Spatulate. Apex: Praemorse, moderately crinkled. Base: Acute. Margin: Entire. Texture, upper and lower surfaces: Smooth, glabrous; velvety. Luster, upper and lower surfaces: Matte. Color: When opening and fully opened, upper surface: Close to between 65D and NN155D; central blotch, close to 60B and towards the base of the blotch, close to 187A to 187B. When opening and fully opened, lower surface: Close to 75B; margins, close to between 65D and NN155D; towards the base, close to 187A to 187B.

*Sepals*.—Quantity and arrangement: About five in a single whorl; proximal 70% portion of the sepals are fused into a campanulate-shaped calyx; epicalyx, free; outer lobes are roughly deltoid in shape with short to medium acuminate apices and inner lobes are roughly deltoid in shape with short acuminate apices. Length: About 2.3 cm. Width, at base of "free" portion: About 7 mm. Shape: Oblong. Apex: Broadly acute. Margin: Entire. Texture, upper and lower surfaces: Smooth, glabrous. Luster, upper and lower surfaces: Matte. Color: When opening, upper surface: Close to 138C. When opening, lower surface: Close to 137C; towards the base, close to 143C. Fully opened, upper surface: Close to 138C. Fully opened, lower surface: Close to 137C; towards the base, close to 144B.

*Peduncles*.—Length: About 6.5 cm. Diameter: About 2 mm. Strength: Strong. Aspect: Erect. Texture: Smooth, glabrous; waxy. Color: Close to N137C; waxy layer, close to 189A.

*Pedicels*.—Length: About 8 mm. Diameter: About 1.5 mm. Strength: Strong. Aspect: About 20° from the peduncle axis. Texture: Smooth, glabrous. Color: Close to N137C; waxy layer, close to 189A.

*Reproductive organs*.—Stamens: Quantity: About two per flower; strongly deformed. Filament length: About 2.1 cm. Filament color: Close to NN155D. Anther length: About 7 mm. Anther shape: Narrowly spatulate to irregularly oblong. Anther color: Close to 64A, 70C and 70D. Pollen: None produced. Pistils: Quantity: About two per flower. Pistil length: About 9 mm. Stigma shape: Pointed, slightly curved. Stigma color: Close to NN155A. Style length: About 8 mm. Style color: Close to 157D. Ovary shape: Obovoid. Ovary texture: Ribbed. Ovary color: Close to 145B; lighter towards the base.

*Fruits and seeds*.—Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be hardy to USDA Hardiness Zone 9.

It is claimed:

1. A new and distinct Carnation plant named 'Hilrees' as illustrated and described.

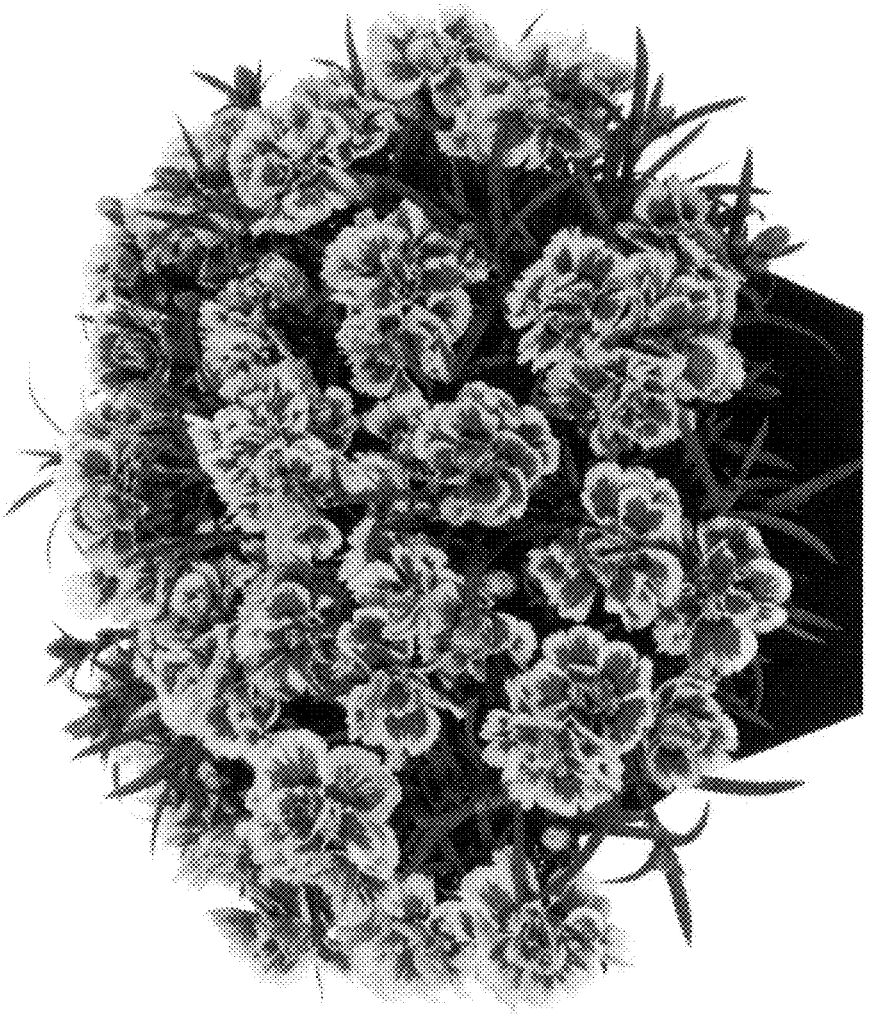

* * * * *